US007053047B2

United States Patent
Peng et al.

(10) Patent No.: US 7,053,047 B2
(45) Date of Patent: May 30, 2006

(54) CYCLIC PENTAPEPTIDES AND THEIR PREPARATION

(75) Inventors: Shigi Peng, Beijing (CN); Ming Zhao, Beijing (CN); Chao Wang, Beijing (CN); Lin Na, Beijing (CN)

(73) Assignee: Purzer Pharmaceutical Co., Ltd., Taipei (TW)

( * ) Notice: Subject to any disclaimer, the term of this patent is extended or adjusted under 35 U.S.C. 154(b) by 466 days.

(21) Appl. No.: 10/404,124

(22) Filed: Apr. 2, 2003

(65) Prior Publication Data

US 2003/0191278 A1 Oct. 9, 2003

(30) Foreign Application Priority Data

Apr. 3, 2002 (TW) .................. 91106708

(51) Int. Cl.
*A61K 38/00* (2006.01)
*A61K 38/12* (2006.01)

(52) U.S. Cl. .......................... 514/9; 530/317
(58) Field of Classification Search .............. None
See application file for complete search history.

(56) References Cited

U.S. PATENT DOCUMENTS 5,514,590 A 5/1996 Garvin et al. ............ 435/320.1

FOREIGN PATENT DOCUMENTS

WO    WO 00/75176 A1 * 12/2000

OTHER PUBLICATIONS

Yin-Ye Wang, Ming Zhao, Shi-Qi Peng, Chang-Ling Li, Qin-Lu Zhou and Qiang Li, "The Antithrombotic Effects of P6A and its Derivatives", Journal of Chinese Pharmaceutical Sciences 1996, 5 (4), pp. 174-176.

* cited by examiner

*Primary Examiner*—Bruce R. Campell
*Assistant Examiner*—Satyanarayana R. Gudibande
(74) *Attorney, Agent, or Firm*—Bacon & Thomas

(57) ABSTRACT

This invention relates to cyclic peptides, with the following formula (I) (SEQ ID NO: 1), cyclo(Xaa-Arg-Pro-Ala-Lys)    (I)

where Xaa is Ala, Gly, Glu, Gln, Asp, Asn, Arg or Lys. The cyclic peptides have thrombolytic effects. This invention also relates to cyclic peptide preparations.

26 Claims, 2 Drawing Sheets

SEQUENCE LISTING

<160> NUMBER OF SEQ ID NOS: 31

<210> SEQ ID NO 1
<211> LENGTH: 5

```
-continued

<212> TYPE: PRT
<213> ORGANISM: Artificial
<220> FEATURE:
<223> OTHER INFORMATION: Formula (I)
<220> FEATURE:
<221> NAME/KEY: Cyclopeptide
<222> LOCATION: (1)..(5)
<223> OTHER INFORMATION: X=A,G,E,Q,D,N,R,K
<220> FEATURE:
<221> NAME/KEY: misc_feature
<222> LOCATION: (1)..(1)
<223> OTHER INFORMATION: Xaa can be any naturally occurring amino acid

<400> SEQUENCE: 1

Xaa Arg Pro Ala Lys
1               5

<210> SEQ ID NO 2
<211> LENGTH: 5
<212> TYPE: PRT
<213> ORGANISM: Artificial
<220> FEATURE:
<223> OTHER INFORMATION: used for cyclopeptide synthesis
<220> FEATURE:
<221> NAME/KEY: PEPTIDE
<222> LOCATION: (1)..(5)
<223> OTHER INFORMATION: X=A,G,E,Q,D,N,R,KN-blocked and side chain
      protected
<220> FEATURE:
<221> NAME/KEY: misc_feature
<222> LOCATION: (1)..(1)
<223> OTHER INFORMATION: Xaa can be any naturally occurring amino acid

<400> SEQUENCE: 2

Xaa Arg Pro Ala Lys
1               5

<210> SEQ ID NO 3
<211> LENGTH: 5
<212> TYPE: PRT
<213> ORGANISM: Artificial
<220> FEATURE:
<223> OTHER INFORMATION: used for cyclopeptide synthesis
<220> FEATURE:
<221> NAME/KEY: PEPTIDE
<222> LOCATION: (1)..(5)
<223> OTHER INFORMATION: X=A,G,E,Q,D,N,R,KN-blocked and side chain
      protected
<220> FEATURE:
<221> NAME/KEY: misc_feature
<222> LOCATION: (5)..(5)
<223> OTHER INFORMATION: Xaa can be any naturally occurring amino acid

<400> SEQUENCE: 3

Arg Pro Ala Lys Xaa
1               5

<210> SEQ ID NO 4
<211> LENGTH: 5
<212> TYPE: PRT
<213> ORGANISM: Artificial
<220> FEATURE:
<223> OTHER INFORMATION: used for cyclopeptide synthesis
<220> FEATURE:
<221> NAME/KEY: PEPTIDE
<222> LOCATION: (1)..(5)
<223> OTHER INFORMATION: X=A,G,E,Q,D,N,R,KN-blocked and side chain
      protected
<220> FEATURE:
<221> NAME/KEY: misc_feature
<222> LOCATION: (4)..(4)
<223> OTHER INFORMATION: Xaa can be any naturally occurring amino acid
```

```
<400> SEQUENCE: 4

Pro Ala Lys Xaa Arg
1               5

<210> SEQ ID NO 5
<211> LENGTH: 5
<212> TYPE: PRT
<213> ORGANISM: Artificial
<220> FEATURE:
<223> OTHER INFORMATION: used for cyclopeptide synthesis
<220> FEATURE:
<221> NAME/KEY: PEPTIDE
<222> LOCATION: (1)..(5)
<223> OTHER INFORMATION: X=A,G,E,Q,D,N,R,KN-blocked and side chain
      protected
<220> FEATURE:
<221> NAME/KEY: misc_feature
<222> LOCATION: (3)..(3)
<223> OTHER INFORMATION: Xaa can be any naturally occurring amino acid

<400> SEQUENCE: 5

Ala Lys Xaa Arg Pro
1               5

<210> SEQ ID NO 6
<211> LENGTH: 5
<212> TYPE: PRT
<213> ORGANISM: Artificial
<220> FEATURE:
<223> OTHER INFORMATION: used for cyclopeptide synthesis
<220> FEATURE:
<221> NAME/KEY: PEPTIDE
<222> LOCATION: (1)..(5)
<223> OTHER INFORMATION: X=A,G,E,Q,D,N,R,KN-blocked and side chain
      protected
<220> FEATURE:
<221> NAME/KEY: misc_feature
<222> LOCATION: (2)..(2)
<223> OTHER INFORMATION: Xaa can be any naturally occurring amino acid

<400> SEQUENCE: 6

Lys Xaa Arg Pro Ala
1               5

<210> SEQ ID NO 7
<211> LENGTH: 5
<212> TYPE: PRT
<213> ORGANISM: Artificial
<220> FEATURE:
<223> OTHER INFORMATION: Compound 1
<220> FEATURE:
<221> NAME/KEY: PEPTIDE
<222> LOCATION: (1)..(5)
<223> OTHER INFORMATION: N-, C-both blockedside chain protected

<400> SEQUENCE: 7

Ala Arg Pro Ala Lys
1               5

<210> SEQ ID NO 8
<211> LENGTH: 5
<212> TYPE: PRT
<213> ORGANISM: Artificial
<220> FEATURE:
<223> OTHER INFORMATION: Compound 2
<220> FEATURE:
<221> NAME/KEY: PEPTIDE
<222> LOCATION: (1)..(5)
<223> OTHER INFORMATION: N-, C-both blockedside chain protected

<400> SEQUENCE: 8
```

Gly Arg Pro Ala Lys
1               5

<210> SEQ ID NO 9
<211> LENGTH: 5
<212> TYPE: PRT
<213> ORGANISM: Artificial
<220> FEATURE:
<223> OTHER INFORMATION: Compound 3
<220> FEATURE:
<221> NAME/KEY: PEPTIDE
<222> LOCATION: (1)..(5)
<223> OTHER INFORMATION: N-, C-both blockedside chain protected

<400> SEQUENCE: 9

Lys Arg Pro Ala Lys
1               5

<210> SEQ ID NO 10
<211> LENGTH: 5
<212> TYPE: PRT
<213> ORGANISM: Artificial
<220> FEATURE:
<223> OTHER INFORMATION: Compound 4
<220> FEATURE:
<221> NAME/KEY: PEPTIDE
<222> LOCATION: (1)..(5)
<223> OTHER INFORMATION: N-, C-both blockedside chain protected

<400> SEQUENCE: 10

Gln Arg Pro Ala Lys
1               5

<210> SEQ ID NO 11
<211> LENGTH: 5
<212> TYPE: PRT
<213> ORGANISM: Artificial
<220> FEATURE:
<223> OTHER INFORMATION: Compound 5
<220> FEATURE:
<221> NAME/KEY: PEPTIDE
<222> LOCATION: (1)..(5)
<223> OTHER INFORMATION: N-, C-both blockedside chain protected

<400> SEQUENCE: 11

Pro Arg Ala Lys Ala
1               5

<210> SEQ ID NO 12
<211> LENGTH: 5
<212> TYPE: PRT
<213> ORGANISM: Artificial
<220> FEATURE:
<223> OTHER INFORMATION: Compound 6
<220> FEATURE:
<221> NAME/KEY: PEPTIDE
<222> LOCATION: (1)..(5)
<223> OTHER INFORMATION: N-, C-both blockedside chain protected

<400> SEQUENCE: 12

Pro Arg Gly Lys Ala
1               5

<210> SEQ ID NO 13
<211> LENGTH: 5
<212> TYPE: PRT
<213> ORGANISM: Artificial
<220> FEATURE:
<223> OTHER INFORMATION: Compound 7

```
<220> FEATURE:
<221> NAME/KEY: PEPTIDE
<222> LOCATION: (1)..(5)
<223> OTHER INFORMATION: N-, C-both blockedside chain protected

<400> SEQUENCE: 13

Pro Arg Lys Lys Ala
1               5

<210> SEQ ID NO 14
<211> LENGTH: 5
<212> TYPE: PRT
<213> ORGANISM: Artificial
<220> FEATURE:
<223> OTHER INFORMATION: Compound 8
<220> FEATURE:
<221> NAME/KEY: PEPTIDE
<222> LOCATION: (1)..(5)
<223> OTHER INFORMATION: N-, C-both blockedside chain protected

<400> SEQUENCE: 14

Pro Arg Gln Lys Ala
1               5

<210> SEQ ID NO 15
<211> LENGTH: 5
<212> TYPE: PRT
<213> ORGANISM: Artificial
<220> FEATURE:
<223> OTHER INFORMATION: Compound 9
<220> FEATURE:
<221> NAME/KEY: PEPTIDE
<222> LOCATION: (1)..(5)
<223> OTHER INFORMATION: N- blocked and side chain protected

<400> SEQUENCE: 15

Ala Arg Pro Ala Lys
1               5

<210> SEQ ID NO 16
<211> LENGTH: 5
<212> TYPE: PRT
<213> ORGANISM: Artificial
<220> FEATURE:
<223> OTHER INFORMATION: Compound 10
<220> FEATURE:
<221> NAME/KEY: PEPTIDE
<222> LOCATION: (1)..(5)
<223> OTHER INFORMATION: N- blocked and side chain protected

<400> SEQUENCE: 16

Pro Arg Ala Lys Ala
1               5

<210> SEQ ID NO 17
<211> LENGTH: 5
<212> TYPE: PRT
<213> ORGANISM: Artificial
<220> FEATURE:
<223> OTHER INFORMATION: Compound 11
<220> FEATURE:
<221> NAME/KEY: PEPTIDE
<222> LOCATION: (1)..(5)
<223> OTHER INFORMATION: N- blocked and side chain protected

<400> SEQUENCE: 17

Gly Arg Pro Ala Lys
1               5
```

```
<210> SEQ ID NO 18
<211> LENGTH: 5
<212> TYPE: PRT
<213> ORGANISM: Artificial
<220> FEATURE:
<223> OTHER INFORMATION: Compound 12
<220> FEATURE:
<221> NAME/KEY: PEPTIDE
<222> LOCATION: (1)..(5)
<223> OTHER INFORMATION: N- blocked and side chain protected

<400> SEQUENCE: 18

Pro Arg Gly Lys Ala
1               5

<210> SEQ ID NO 19
<211> LENGTH: 5
<212> TYPE: PRT
<213> ORGANISM: Artificial
<220> FEATURE:
<223> OTHER INFORMATION: Compound 13
<220> FEATURE:
<221> NAME/KEY: PEPTIDE
<222> LOCATION: (1)..(5)
<223> OTHER INFORMATION: N- blocked and side chain protected

<400> SEQUENCE: 19

Lys Arg Pro Ala Lys
1               5

<210> SEQ ID NO 20
<211> LENGTH: 4
<212> TYPE: PRT
<213> ORGANISM: Artificial
<220> FEATURE:
<223> OTHER INFORMATION: Compound 14
<220> FEATURE:
<221> NAME/KEY: PEPTIDE
<222> LOCATION: (1)..(4)
<223> OTHER INFORMATION: N- blocked and side chain protected

<400> SEQUENCE: 20

Pro Arg Lys Ala
1

<210> SEQ ID NO 21
<211> LENGTH: 5
<212> TYPE: PRT
<213> ORGANISM: Artificial
<220> FEATURE:
<223> OTHER INFORMATION: Compound 15
<220> FEATURE:
<221> NAME/KEY: PEPTIDE
<222> LOCATION: (1)..(4)
<223> OTHER INFORMATION: N- blocked and side chain protected

<400> SEQUENCE: 21

Gln Arg Pro Ala Lys
1               5

<210> SEQ ID NO 22
<211> LENGTH: 5
<212> TYPE: PRT
<213> ORGANISM: Artificial
<220> FEATURE:
<223> OTHER INFORMATION: Compound 16
<220> FEATURE:
<221> NAME/KEY: PEPTIDE
<222> LOCATION: (1)..(4)
<223> OTHER INFORMATION: N- blocked and side chain protected
```

```
<400> SEQUENCE: 22

Pro Arg Gln Lys Ala
1               5

<210> SEQ ID NO 23
<211> LENGTH: 5
<212> TYPE: PRT
<213> ORGANISM: Artificial
<220> FEATURE:
<223> OTHER INFORMATION: Compound 17
<220> FEATURE:
<221> NAME/KEY: CYCLOPEPTIDE
<222> LOCATION: (1)..(5)
<223> OTHER INFORMATION: side chain protected

<400> SEQUENCE: 23

Ala Arg Pro Ala Lys
1               5

<210> SEQ ID NO 24
<211> LENGTH: 5
<212> TYPE: PRT
<213> ORGANISM: Artificial
<220> FEATURE:
<223> OTHER INFORMATION: Compound 18
<220> FEATURE:
<221> NAME/KEY: CYCLOPEPTIDE
<222> LOCATION: (1)..(5)
<223> OTHER INFORMATION: side chain protected

<400> SEQUENCE: 24

Gly Arg Pro Ala Lys
1               5

<210> SEQ ID NO 25
<211> LENGTH: 5
<212> TYPE: PRT
<213> ORGANISM: Fibrinogen beta
<220> FEATURE:
<221> NAME/KEY: PEPTIDE
<222> LOCATION: (1)..(5)
<300> PUBLICATION INFORMATION:
<301> AUTHORS: Belew M, Gerdin B, Lindeberg G, Porath J, Saldeen T,
       Wallin R.
<302> TITLE: Structure-activity relationships of vasoactive peptides
       derived from fibrin or fibrinogen degraded by plasmin
<303> JOURNAL: Biochim Biophys Acta.
<304> VOLUME: 621
<305> ISSUE: 2
<306> PAGES: 169-178
<307> DATE: 1980-02-27
<308> DATABASE ACCESSION NUMBER: Pubmed
<309> DATABASE ENTRY DATE: 2003-03-26
<313> RELEVANT RESIDUES: (1)..(5)

<400> SEQUENCE: 25

Ala Arg Pro Ala Lys
1               5

<210> SEQ ID NO 26
<211> LENGTH: 5
<212> TYPE: PRT
<213> ORGANISM: Artificial
<220> FEATURE:
<223> OTHER INFORMATION: GP6A
<220> FEATURE:
<221> NAME/KEY: PEPTIDE
<222> LOCATION: (1)..(5)

<400> SEQUENCE: 26
```

```
Gly Arg Pro Ala Lys
1               5

<210> SEQ ID NO 27
<211> LENGTH: 5
<212> TYPE: PRT
<213> ORGANISM: Artificial
<220> FEATURE:
<223> OTHER INFORMATION: KP6A
<220> FEATURE:
<221> NAME/KEY: PEPTIDE
<222> LOCATION: (1)..(5)

<400> SEQUENCE: 27

Lys Arg Pro Ala Lys
1               5

<210> SEQ ID NO 28
<211> LENGTH: 5
<212> TYPE: PRT
<213> ORGANISM: Artificial
<220> FEATURE:
<223> OTHER INFORMATION: QP6A
<220> FEATURE:
<221> NAME/KEY: PEPTIDE
<222> LOCATION: (1)..(5)

<400> SEQUENCE: 28

Gln Arg Pro Ala Lys
1               5

<210> SEQ ID NO 29
<211> LENGTH: 5
<212> TYPE: PRT
<213> ORGANISM: Artificial
<220> FEATURE:
<223> OTHER INFORMATION: Cyclo P6A
<220> FEATURE:
<221> NAME/KEY: CYCLOPEPTIDE
<222> LOCATION: (1)..(5)

<400> SEQUENCE: 29

Ala Arg Pro Ala Lys
1               5

<210> SEQ ID NO 30
<211> LENGTH: 5
<212> TYPE: PRT
<213> ORGANISM: Artificial
<220> FEATURE:
<223> OTHER INFORMATION: Cyclo GP6A
<220> FEATURE:
<221> NAME/KEY: CYCLOPEPTIDE
<222> LOCATION: (1)..(5)

<400> SEQUENCE: 30

Gly Arg Pro Ala Lys
1               5

<210> SEQ ID NO 31
<211> LENGTH: 5
<212> TYPE: PRT
<213> ORGANISM: Artificial
<220> FEATURE:
<223> OTHER INFORMATION: Cyclo KP6A
<220> FEATURE:
<221> NAME/KEY: CYCLOPEPTIDE
<222> LOCATION: (1)..(5)

<400> SEQUENCE: 31
```

```
Lys Arg Pro Ala Lys
1             5
```

CYCLIC PENTAPEPTIDES AND THEIR PREPARATION

BACKGROUND OF THE INVENTION

1. Field of the Invention

The present invention relates to a novel cyclic peptide and its preparation.

2. Description of Related Art

Peptide 6A is a degradation of fibrinogen β chain analogue which has been known to increase coronary artery and femoral artery blood flow. In 1978(1), peptide 6A was first isolated and purified from the β chain of human fibrinogen by Belew et al.(2). The composition of peptide 6A was confirmed as Ala-Arg-Pro-Ala-Lys (SEQ ID NO: 25). This peptide increases coronary artery and femoral artery blood flow in dogs. In 1997, the inventors prepared peptide 6A and its analogues by solution method and observed that these peptides have good potency for relaxing vascula, lowering blood pressure and anti-thrombosis. The synthetic techniques and functions of these compounds have been described in CN Patent No. 1146458. However, in 1990, the inventors observed that peptide 6A had no additional benefit on the parameters of thrombolysis when injected intravenously (i.v.) together with tissue plasminogene activator in dogs with coronary artery thrombosis. The results indicated that peptide 6A might be degraded rapidly by angiotensin-converting enzyme (ACE) in lung during intravenous administration since peptide 6A is the substrate of this enzyme. In addition, peptide 6A and its analogues, which were synthesized by the inventors in 1997, had excellent anti-thrombosis ability, but their half-life in vivo was quite short, consequently unable to exhibit long-term potency.

In order to solve the problems described above, the inventors considered that a cyclic peptide usually has the characteristic of restricted conformations afford good stability toward peptidase. Therefore, the inventors tried to synthesize peptide 6A and its analogues as cyclic forms to avoid degradation caused by ACE; moreover, so that the cyclic compounds will not lose thrombolytic effects. At this moment, a new cyclic compound and also a new technique to convert linear peptide 6A and its analogues to cyclic forms are needed.

SUMMARY OF THE INVENTION

It is one object of the present invention to provide novel cyclic peptides that have long-term thrombolytic potency.

It is another object of the present invention to provide a method for preparing novel cyclic peptides describes above.

According to the present invention, it is provided a novel cyclic peptide of the following formula (I) (SEQ ID NO: 1):

cyclo(Xaa-Arg-Pro-Ala-Lys)    (I)

wherein Xaa is Ala, Gly, Glu, Gln, Asp, Asn, Arg or Lys.

The formula (I) (SEQ ID NO: 1) cyclic peptide can be synthesized by the following method 1 or method 2.

Method 1:

First, at least one peptide with an N-terminal protecting group is provided, wherein said peptide is selected from the group consisting of:
B-Xaa-Arg(T)-Pro-Ala-Lys(Z')-OH (SEQ ID NO: 2),
B-Arg(T)-Pro-Ala-Lys(Z')-Xaa-OH (SEQ ID NO: 3),
B-Pro-Ala-Lys(Z')-Xaa-Arg(T)-OH (SEQ ID NO: 4),
B-Ala-Lys(Z')-Xaa-Arg(T)-Pro-OH (SEQ ID NO: 5), and
B-Lys(Z')-Xaa-Arg(T)-Pro-Ala-OH (SEQ ID NO: 6);
wherein Xaa is Ala, Gly, Glu, Gln, Asp, Asn, Arg or Lys; B is N-terminal protecting group of the peptide chain; Z' is the side chain protecting group of Lys residue; and T is the side chain protecting group of Arg residue.

p-Nitrophenol, an adequate organic solvent and a coupling agent were then added to activate the C-terminal group of said peptide and to form a first intermediate.

After that, the N-terminal protecting group was removed from the first intermediate to form a second intermediate.

The second intermediate is dissolved in an appropriate organic solvent and undergoes a cycloaddition reaction to form a third intermediate.

Finally, the side chain protecting groups of Lys and Arg residues were removed from the third intermediate to form the final product.

Method 2:

First, a peptide with an N-terminal protecting group is provided, wherein said peptide is selected from the group consisting of:
B-Xaa-Arg(T)-Pro-Ala-Lys(Z')-OH (SEQ ID NO: 2),
B-Arg(T)-Pro-Ala-Lys(Z')-Xaa-OH (SEQ ID NO: 3),
B-Pro-Ala-Lys(Z')-Xaa-Arg(T)-OH (SEQ ID NO: 4),
B-Ala-Lys(Z')-Xaa-Arg(T)-Pro-OH (SEQ ID NO: 5), and
B-Lys(Z')-Xaa-Arg(T)-Pro-Ala-OH (SEQ ID NO: 6);

wherein Xaa is Ala, Gly, Glu, Gln, Asp, Asn, Arg or Lys; B is the N-terminal protecting group of peptide chain; Z' is the side chain protecting group of Lys residue; and T is the side chain protecting group of Arg residue.

The N-terminal protecting group of said peptide was then removed to form a first intermediate.

The first intermediate was dissolved in an appropriate organic solvent, and a coupling agent was subsequently added to perform direct coupling reaction, which provides a second intermediate.

Finally, the protecting groups on the side chain of the Lys and Arg residues of the second intermediate were removed to form the cyclic peptide as formula (I).

The formula (I) cyclic peptide has a thrombolytic potency, and the peptides therefore can be used as a drug for relaxing blood vessel, lowering blood pressure and anti-thrombosis, and can be further applied to treat thrombosis, hypertension, and myocardial infarction.

DETAILED DESCRIPTION OF THE INVENTION

Figure 1:
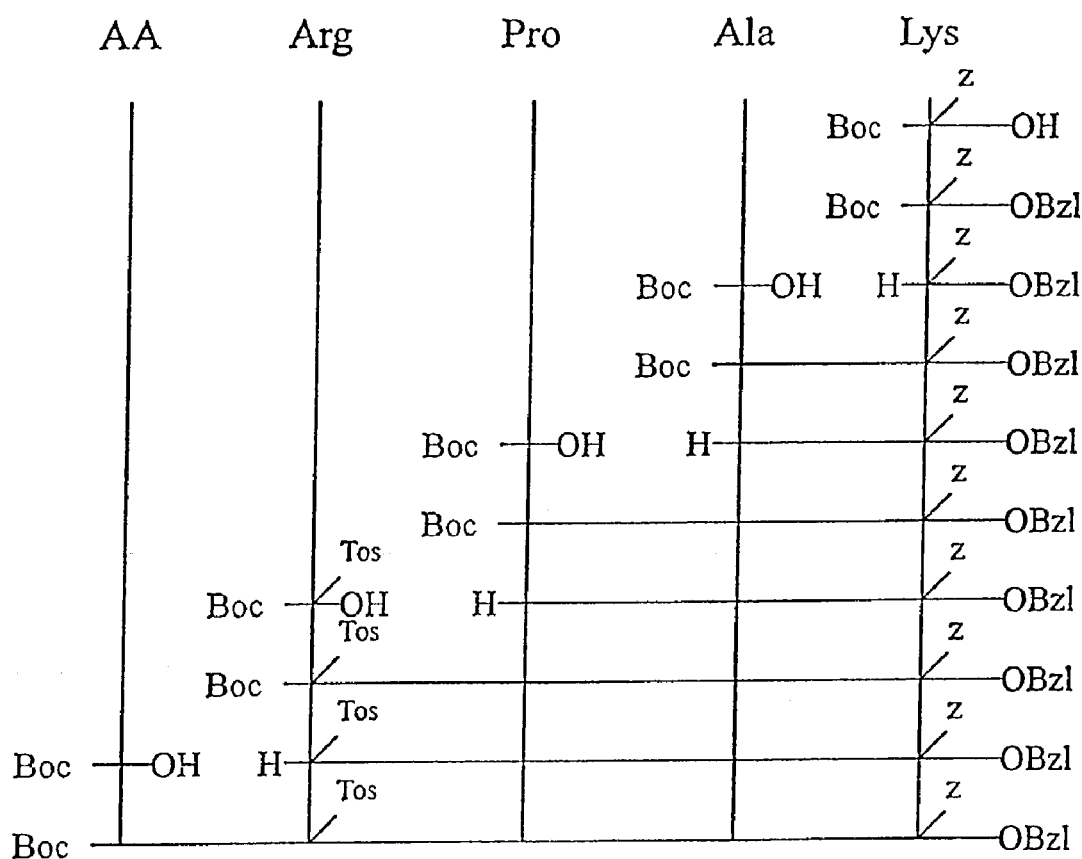
FIG. 1 shows P6A (SEQ ID NO: 25) and P6A analogue synthesis path, wherein AA represents the corresponding protected L-Ala, Gly, L-Lys, and L-Gln.

The present invention provides a method to converse the linear peptide 6A and its analogues into cyclic structures whose backbone conformation mobility is restricted. Thus, the degradation rate of cyclic peptide of the present invention decreases dramatically and therefore its half-life in vivo will be prolonged.

In the present invention, peptides 6A and the analogues, respectively, are prepared by solid phase or solution phase synthesis. The corresponding cyclic pentapeptide is also prepared by the same methods. The thrombolytic effect was evaluated on a rat model of thrombolysis.

The present invention provides a cyclic peptide of the following formula (I) (SEQ ID NO: 1):

cyclo(Xaa-Arg-Pro-Ala-Lys)    (I)

wherein the Xaa is Ala, Gly, Glu, Gln, Asp, Asn, Arg, or Lys.

The formula (I) cyclic peptide can be prepared by solid phase or liquid phase synthesis method.

The following linear pentapeptide groups are prepared through conventional solid phase or solution synthesis method, using an amino acid comprising an L-protecting group as the starting material:

B-Xaa-Arg(T)-Pro-Ala-Lys(Z')-OH (SEQ ID NO: 2),
B-Arg(T)-Pro-Ala-Lys(Z')-Xaa-OH (SEQ ID NO: 3),
B-Pro-Ala-Lys(Z')-Xaa-Arg(T)-OH (SEQ ID NO: 4),
B-Ala-Lys(Z')-Xaa-Arg(T)-Pro-OH (SEQ ID NO: 5),
B-Lys(Z')-Xaa-Arg(T)-Pro-Ala-OH (SEQ ID NO: 6);

wherein the Xaa is Ala, Gly, Glu, Gln, Asp, Asn, Arg, or Lys; B is the N-terminal protecting group of peptide chain; Z' is the side chain protecting group of Lys residue; and T is the side chain protecting group of Arg residue. The protecting group B described above is a conventional N-terminal protecting group, and preferably selected from a group comprising Boc, Fmoc, Z, Adoc, Bpoc, Trt, and Nps; at least one protecting group Z on the side chain of Lys residue is selected form the group comprising 4-ClZ, 2-ClZ, 2,4-Cl$_2$Z, 3,4-Cl$_2$Z, 3-ClZ, 2,6Cl$_2$Z, Boc, Tos and Cu; and, at least one protecting group T on the side chain of Arg residue is selected from the group comprising Tos, No$_2$, Z, Z$_2$, Mbs, Mts (2,4,6-trimethylbenzosulfidyl), Boc, and Adoc.

The linear pentapeptides described above are used as starting materials to perform cyclization. The present invention for the fist time discloses two cyclization methods applicable to the linear pentapeptides described above. The first is called "p-nitrophenol ester method", which uses p-nitrophenol as an activator to activate the inert —COOH group on the C-terminus of peptide chain. A labile —COONp group are thus obtained and then the intramolecular cyclization occurs naturally. The later one is called "direct coupling method", using coupling agents to perform cyclization under appropriate conditions. The details of the two methods are described as follows.

1. p-Nitrophenol Ester Method

Linear pentapeptides comprising an N-terminal protecting group as described above are provided. p-Nitrophenol, proper organic solvents and a coupling agent are added to activate the C-terminal group of the peptides and a first intermediate forms; wherein the organic solvents are not limited, preferably at least one is selected from the group comprising THF, Dioxane, DMF, DMSO, ethyl acetate, dichloromethane, and trichloromethane; the coupling agents are conventional ones used in amino acid synthesis, preferably at least one is selected from the group comprising DCC, HOBt, HONb, HOSu, and p-nitrophenol. An example of the first intermediate is Boc-Xaa-Arg(T)-Pro-Ala-Lys(Z')-ONp, and the rest can be conceived by those skilled in the art.

The N-terminal protecting group of first intermediate was then removed by reacting a deprotecting agent and the first intermediate to form a second intermediate; wherein the choices of deprotecting agents depend on the N-terminal protecting groups, based on the prior arts, preferably at least one is selected from the group comprising HCl/ethyl acetate, HCl/dichlorocyclohexane, trifluoroacetatic acid, H$_2$/Pd, C, and pyridine. An example of the first intermediate is HCl-Xaa-Arg(T)-Pro-Ala-Lys(Z')-ONp, and the rest can be conceived by those skilled in the art.

The second intermediate is then dissolved in proper organic solvents and undergoes cyclization to form a third intermediate; wherein the organic solvents are as described above, and the cyclization is performed by adding at least one agent selected from the group comprising Na$_2$CO$_3$, NaHCO$_3$, K$_2$CO$_3$, KHCO$_3$, TEA, NH$_3$, NMM, and N(C$_2$H$_5$)$_3$ so that C-terminus and N-terminus on the peptide chain react with each other, thus the O, Np, or ONp group leaving naturally, and form a cyclic compound. An example of third intermediate is cyclo(Xaa-Arg(T)-Pro-Ala-Lys(Z')). It should be noticed that from the beginning step to the present step, all the side chains on the Arg and Lys residue of intermediate have protecting groups.

Therefore, the side chain protecting groups on Lys and Arg residue should be removed to form the final compound. The deprotecting reaction is performed by reacting the third intermediate with the second deprotecting agents, wherein the second deprotecting agents are selected according to the desired deprotecting group, preferably at least one is selected from hydrofluoric acid, triflouroacetatic acid, trifluoromethyl sulfonic acid, H$_2$/Pd, and C. A final compound example is cyclo(Xaa-Arg-Pro-Ala-Lys) (SEQ ID NO: 1), and the rest can be conceived by those skilled in the art.

2. Direct Coupling Method

A linear peptide having an N-terminal protecting group as described above is provided. The N-terminal protecting group was removed by reacting with a first deprotecting agent to form a first intermediate, wherein the first deprotecting agent is selected according to the N-terminal protecting group, and preferably selected from the group comprising HCl/ethyl acetate, HCl/dichlorocyclohexane, trifluoroacetatic acid, H$_2$/Pd, C, and pyridine. An example of the first intermediate is HCl-Xaa-Arg(T)-Pro-Ala-Lys(Z')-OH, and the rest can be conceived by those skilled in the art.

The first intermediate is then dissolved in proper organic solvents, and coupling agents are added to perform a coupling reaction which results in providing a second intermediate; wherein the organic solvents are not specified, preferably at least one is selected from the group comprising anhydrous THF, dioxane, DMF, DMSO, ethyl acetate, and dichloromethane; the coupling agents are those used in conventional amino acids synthesis, preferably at least one selected from the group comprising DCC, HOBt, HONb, HOSu, and p-nitrophenol. The pH value of reaction preferably ranges from 6.0 to 8.0. The reaction temperature preferably ranges from 50° C. to 90° C.; and the pH value is adjusted by alkali, preferably at least one of which is selected from the group comprising Na$_2$CO$_3$, NaHCO$_3$, K$_2$CO$_3$, TEA, NH$_3$, and NMM. The cyclization is completed at this step, and a second intermediate example is cyclo(Xaa-Arg(T)-Pro-Ala-Lys(Z')), and the rest can be conceived by those skilled in the art.

As described above, there are still protecting groups attached to side chains on Arg and Lys residue of the cyclic compounds. Thus, the protecting groups on Arg and Lys residue of the final compound should be removed and the method is as described above. A final compound example is cyclo(Xaa-Arg-Pro-Ala-Lys) (SEQ ID NO: 1), and the rest can be conceived by those skilled in the art.

DETAILED DESCRIPTION OF THE PREFERRED EMBODIMENT

Chemical Synthesis

Reactant Preparation

L-protected amino acids, DCC and HOBt were purchased from Sigma Chemical Co.; anhydrous THF was distilled from Na under normal temperatures; Dry DMF and dioxane were distilled from calcium chloride and treated with 4A molecular sieve; linear peptides were prepared by a solution method utilizing Boc chemistry. DCC was used as a coupling agent both in linear and cyclic peptide synthesis; the reaction was monitored by ninhydrin reactions, and the Boc protecting group was removed by 4–6 mol/L HCl/EtOAc. Chromatography was performed on Qingdao Silica gel H. Melting points were determined with a microscopic hostage apparatus, and were uncorrected.

ESI-Mass spectra were obtained on ES-S989X-HO; optical rotation was determined on Polartronic-D polarimeter of Schmidt+Haensch Company.

1. The Preparation of the Following Compounds (1) to (4):

```
                                       (SEQ ID NO: 7)
    Boc-Ala-Arg(Tos)-Pro-Ala-Lys(Z')OBzl        (1)

(SEQ ID NO: 8)
    Boc-Gly-Arg(Tos)-Pro-Ala-Lys(Z')OBzl        (2)

(SEQ ID NO: 9)
    Boc-Lys(Z')-Arg(Tos)-Pro-Ala-Lys(Z')OBzl    (3)

(SEQ ID NO: 10)
    Boc-Gln-Arg(Tos)-Pro-Ala-Lys(Z')OBzl        (4)
```

General procedure of compounds (1) to (4) (SEQ ID NO: 7–10) synthesis: Beginning with Boc protected lysine, using DCC/HOBt as a coupling agent, and utilizing a solution method to elongate the peptide chain. The synthetic route was outlined in scheme 1, see FIG. 1. Detailed descriptions are as follows.

First, the benzyl(Bzl) protecting group is attached to the Boc-protected lysine's C-terminus. The reaction is:

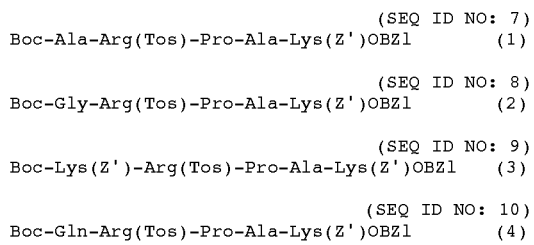

(i)

(ii)

The N-terminal Boc protecting group is then removed, and Boc-Ala and DCC are subsequently added to perform polymerization. The reaction is:

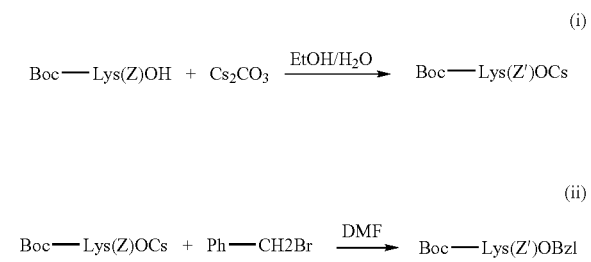

(iii)

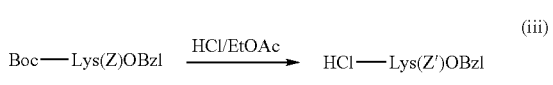

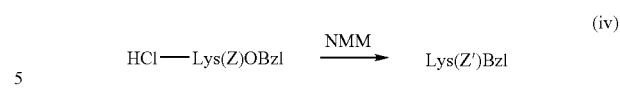

(iv)

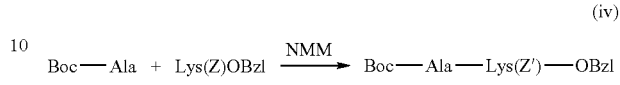

(iv)

Repeat steps (iii) and (iv), and Boc-Pro is added to complete step (v) to form tripeptides. Compounds (1) (SEQ ID NO: 7) to (4) (SEQ ID NO: 10) are prepared by similar schemes.

The physical data of compounds (1) (SEQ ID NO: 7) to (4) (SEQ ID NO: 10) are listed as follows:

Compound (1) (SEQ ID NO: 7), yield, 88%, mp 84–85° C. $[\alpha]_D^{20}$-33 (C2, $CHCl_3$), FAB-MS (m/e) 1020[M+1]$^+$;

Compound (2) (SEQ ID NO: 8), yield, 82%, mp 76–77° C. $[\alpha]_D^{20}$-43 (C2, $CHCl_3$), FAB-MS (m/e) 1211[M+1]$^+$, 1028[M+Na]$^+$;

Compound (3) (SEQ ID NO: 9), yield, 78%, mp 72–74° C. $[\alpha]_D^{20}$-46 (C2, $CHCl_3$), FAB-MS (m/e) 1211[M+1]$^+$;

Compound (4) (SEQ ID NO: 10), yield, 87%, mp 83–85° C. $[\alpha]_D^{20}$-9 (C0.3, $CHCl_3$), FAB-MS (m/e) 1077[M+1]$^+$.

2. The Preparation of Compounds (5) to (8):

```
                                       (SEQ ID NO: 11)
    Boc-Pro-Arg(Tos)-Ala-Lys(Z')-AlaOBzl        (5)

(SEQ ID NO: 12)
    Boc-Pro-Arg(Tos)-Gly-Lys(Z')-AlaOBzl        (6)

(SEQ ID NO: 13)
    Boc-Pro-Arg(Tos)-Lys(Z')-Lys(Z')-AlaOBzl    (7)

(SEQ ID NO: 14)
    Boc-Pro-Arg(Tos)-Gln-Lys(Z')-AlaOBzl        (8)
```

Figure 2:
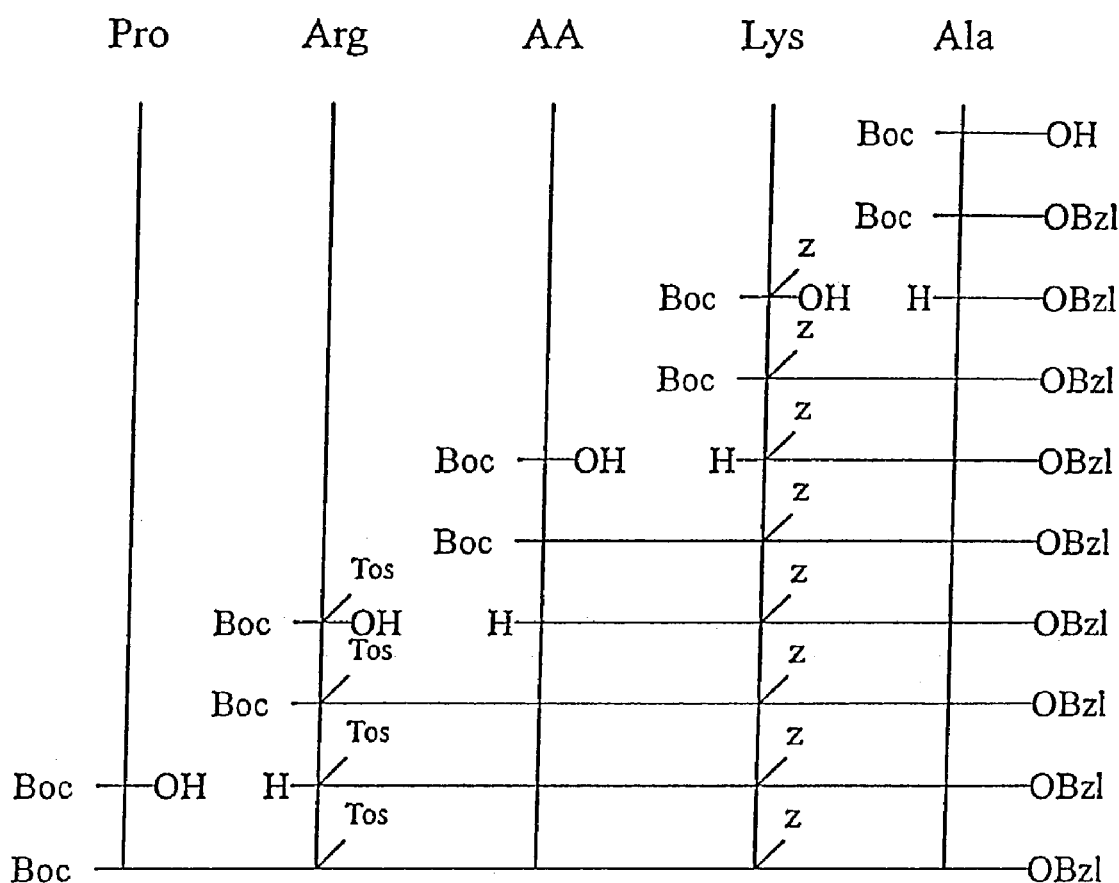
FIG. 2 shows the Compound (5–8) (SEQ ID NO: 11–14) synthesis path, wherein AA represents the corresponding protected L-Ala, Gly, Lys, and Gln.

General procedure of compounds (5) (SEQ ID NO: 11) to (8) (SEQ ID NO: 14) synthesis: Beginning with Boc protected alanine, using DCC/HOBt as a coupling agent, and utilizing a solution method to elongate the peptide chain. The synthetic route was outlined in scheme 2, see FIG. 2.

The physical data of the compounds (5) (SEQ ID NO: 11) to (8) (SEQ ID NO: 14) are listed as follows:

Compound (5) (SEQ ID NO: 11), yield, 68%, mp 146–148° C. $[\alpha]_D^{20}$-22 (C0.5, $CHCl_3$), TOF-MS (m/e) 1020[M+1]$^+$, 1041[M+Na]$^+$, 1058[M+K]$^+$;

Compound (6) (SEQ ID NO: 12), yield, 72%, mp 78–80° C. $[\alpha]_D^{20}$-22 (C1, $CHCl_3$), TOF-MS (m/e) 1006[M+1]$^+$, 1028[M+Na]$^+$, 1044[M+K]$^+$;

Compound (7) (SEQ ID NO: 13), yield, 62%, mp 80–82° C. $[\alpha]_D^{20}$-27 (C0.5, $CHCl_3$), TOF-MS (m/e) 1211[M+1]$^+$, 233[M+Na]$^+$, 1249[M+K]$^+$;

Compound (8) (SEQ ID NO: 14), yield, 78%, mp 90–92° C. $[\alpha]_D^{20}$-24 (CO0.2, $CHCl_3$), TOF-MS (m/e) 1077[M+1]$^+$;

3. The Preparation of Compounds (9) (SEQ ID NO: 15) to (16) (SEQ ID NO: 22):

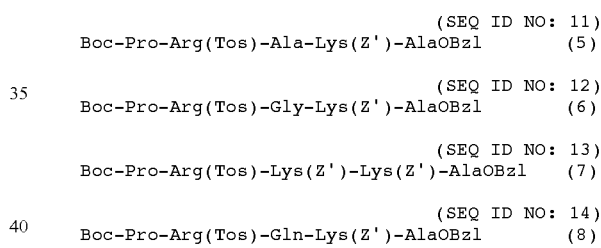

```
                                       (SEQ ID NO: 15)
    Boc-Ala-Arg(Tos)-Pro-Ala-Lys(Z')OH          (9)
```

-continued

```
                                          (SEQ ID NO: 16)
  Boc-Pro-Arg(Tos)-Ala-Lys(Z')-AlaOH          (10)

(SEQ ID NO: 17)
  Boc-Gly-Arg(Tos)-Pro-Ala-Lys(Z')OH          (11)

(SEQ ID NO: 18)
  Boc-Pro-Arg(Tos)-Gly-Lys(Z')-AlaOH          (12)

(SEQ ID NO: 19)
  Boc-Lys(Z')-Arg(Tos)-Pro-Ala-Lys(Z')OH      (13)

(SEQ ID NO: 20)
  Boc-Pro-Arg(Tos)-Lys(Z')-AlaOH              (14)

(SEQ ID NO: 21)
  Boc-Gln-Arg(Tos)-Pro-Ala-Lys(Z')OH          (15)

(SEQ ID NO: 22)
  Boc-Pro-Arg(Tos)-Gln-Lys(Z')-AlaOH          (16)
```

A methanol solution of 0.2 mmol compounds (5,6,7,8) (SEQ ID NO: 11, 12, 13, 14)was cooled in an ice-water bath, 2.0 ml of 2 mol/L NaOH was added dropwise with stirring. The reaction mixture was stirred for 30 min. When thin layer chromatography (TLC) indicated that the reaction was complete, the solution was neutralized with 2 mol/L HCl. After removal of methanol the mixture was filtered, and the filtrate was washed with water for several times, then the filtrate was put in a drier for overnight.

4. Cyclo[Ala-Arg(Tos)-Pro-Ala-Lys(Z')] (17) (SEQ ID NO: 23) Preparation

Method 1: p-nitrophenol Ester Method 0.2 mmol Boc-Ala-Arg(Tos)-Pro-Ala-Lys(Z')OH (SEQ ID NO: 15) and 0.3 mmol p-nitrophenol were dissolved in anhydrous THF(5 ml), cooled in an ice water bath, 0.3 mmol DCC was added and stirred for 3 h, then the reaction was increased to room temperature. 18 h later the mixture was filtered and the solvent was evaporated to dryness in vacuo. The residue was triturated with ethyl ether and a yellow Boc-Ala-Arg(Tos)-Pro-Ala-Lys(Z')ONp powder was obtained. After removing Boc with 4N HCl/EtOAc, the obtained Hcl-Ala-Arg(Tos)-Pro-Ala-Lys(Z')ONp was dissolved in 12 ml dioxane, 2 ml 0.1 mol/L $Na_2CO_3$ and 2 ml 0.1 mol/L $NaHCO_3$ were added and stirred for 2 h. After the solvent was removed, the residue was purified by chromatography to afford the desired product 8 mg (5%), mp 118–120° C., $[\alpha]_D^{20}$-21 (C0.2, $CHCl_3$), TOF-MS(m/e) 812 $[M+1]^+$.

Method 2: Direct Coupling Method

Boc was removed from 0.2 mmol Boc-Ala-Arg(Tos)-Pro-Ala-Lys(Z')OH (SEQ ID NO: 15) with 4N Hcl/EtOAc and the obtained Hcl-Ala-Arg(Tos)-Pro-Ala-Lys(Z')OH was dissolved in 200 ml dry DMF($10^{-3}$M), NMM was added to bring the solution to PH 7, 1 mmol DCC was added and the mixture was stirred at 70° C. for 3 days. The solvent was evaporated in vacuo, the residue was purified by chromatography to afford the desired product 29 mg (18%), the other physical data were the same as method 1.

Method 3: Proline and Alanine as Coupling Sites

Boc was removed from 0.2 mmol. Boc-Pro-Arg(Tos)-Ala-Lys(Z')-AlaOH(10) (SEQ ID NO: 16), and OH-Pro-Arg(Tos)-Ala-Lys(Z')-AlaOH was then dissolved in 200 ml DMF($10^{-3}$M), the procedure was followed as in method 2 to obtain the product. Product data were the same as method 1 and 2 except the yield was 9%.

5. Cyclo[Gly-Arg(Tos)-Pro-Ala-Lys(Z')] (18) (SEQ ID NO: 24) Preparation

Method 1: Direct Coupling Method

Boc was removed from 0.2 mmol Boc-Gly-Arg(Tos)-Pro-Ala-Lys(Z')OH (SEQ ID NO: 17) with 4N Hcl/EtOAc. The obtained HCl-Gly-Arg(Tos)-Pro-Ala-Lys(Z')OH was dissolved in 200 ml dry DMF($10^{-3}$M) and the following procedure was the same as method 2 Cyclo[Ala-Arg(Tos)-Pro-Ala-Lys(Z')] (17) (SEQ ID NO: 23) preparation. The desired product yield was 31%, mp 102–104° C., $[\alpha]_D^{20}$-30(Cl, $CHCl_3$), ESI-MS(m/e), 798$[M+1]^+$, 820$[M+Na]^+$.

Method 2: Proline and Glycine as Coupling Sites

Boc was removed from 0.2 mmol Boc-Gly-Arg(Tos)-Pro-Ala-Lys(Z')OH(12) (SEQ ID NO: 18) and the following synthetic procedure was the same as method 1. The yield was 29% and other physical data were the same as obtained in method 1.

6. Compound (P6A, GP6A, KP6A, QP6A, Cyclo P6A, Cyclo GP6A, and KP6A) Preparation:

```
  H-Ala-Arg-Pro-Ala-LysOH       (19)  (SEQ ID NO: 25)
  (P6A)

H-Gly-Arg-Pro-Ala-LysOH       (20)  (SEQ ID NO: 26)
  (GP6A)

H-Lys-Arg-Pro-Ala-LysOH       (21)  (SEQ ID NO: 27)
  (KP6A)

H-Gln-Arg-Pro-Ala-LysOH       (22)  (SEQ ID NO: 28)
  (QP6A)

Cyclo(Ala-Arg-Pro-Ala-Lys)    (23)  (SEQ ID NO: 29)
  (Cyclo P6A)

Cyclo(Gly-Arg-Pro-Ala-Lys)    (24)  (SEQ ID NO: 30)
  (Cyclo GP6A)

Cyclo(Lys-Arg-Pro-Ala-Lys)    (25)  (SEQ ID NO: 31)
  (Cyclo KP6A)
```

Compound 1, 2, 3, 4, 17, 18 or 21 (SEQ ID NO: 7, 8, 9, 10, 23, 24, 27) was respectively subjected in the reaction vessel and mixed with 1 ml thioether, 1 ml thioanisole and 1 ml of anisole. The mixture was cooled with liquid $N_2$ and liquid anhydrous HF (2 ml) was added and stirred at 0° C. for 60 min. The mixture was then dried in vacuo and the crude product was precipitated by addition of ethyl ether. The precipitate was desalted on Sephadex G 10 using water as eluent and collected by ninhydrin reaction. The collection was lyophilized and white power was obtained. The related data were as follows:

Compound (19) (SEQ ID NO: 25), yield, 80%, mp 168–170° C. $[\alpha]_D^{20}$-44 (C2, $H_2O$), FAB-MS (m/e) 542$[M+1]^+$;

Compound (20) (SEQ ID NO: 26), yield, 78%, mp 168–171° C. $[\alpha]_D^{20}$-81 ($C_1$, $H_2O$), FAB-MS (m/e) 528$[M+1]^+$;

Compound (21) (SEQ ID NO: 27), yield, 82%, mp 138–140° C. $[\alpha]_D^{20}$-65 ($C_1$, $H_2O$), FAB-MS (m/e) 597$[M+1]^+$;

Compound (22) (SEQ ID NO: 28), yield, 80%, mp 180–182° C. $[\alpha]_D^{20}$-65 ($C_1$, $H_2O$), FAB-MS (m/e) 599$[M+1]^+$;

Compound (23) (SEQ ID NO: 29), yield, 53%, mp 196–200° C. $[\alpha]_D^{20}$-64 (C0.5, $H_2O$), ESI-MS (m/e) 524$[M+1]^+$;

Compound (24) (SEQ ID NO: 30), yield, 64%, mp 138–140° C. $[\alpha]_D^{20}$-67 (C0.5, $H_2O$), TOF-MS (m/e) 510$[M+1]^+$;

Compound (25) (SEQ ID NO: 31), yield, 60%, mp 170–174° C. $[\alpha]_D^{20}$-61 (C0.5, $H_2O$), TOF-MS (m/e) 581$[M+1]^+$.

B. Thrombolytic Effect

The thrombolytic effect was evaluated by thrombolysis rat model. Among the 8 compounds, as following description, GP6A (SEQ ID NO: 26) and cyclic GP6A (SEQ ID NO: 30) have much more thrombolytic potency than the others.

1. Thrombus Preparation 0.1 ml Wistar rat blood was poured into a glass tube (length, 15 mm; external diameter, 5.0 mm; internal diameter, 2.5 mm) which was fixed vertically and the bottom was sealed with a rubber stopper. A stainless steel bolt was inserted quickly, the bolt diameter was 0.2 mm and the length was 12 mm. 15 min later, the bolt containing thrombus was taken out from the glass tube and weighed exactly.

2. Thrombolytic Effect of Various Peptides

Male Wistar rat weighing 220 g–280 g were anesthetized with pentobarbital sodium (80 mg/kg, i.p). The right arteria carotis communis and the left vena jugulars externa were separated. The bolt containing thrombus was put in the polyethylene tube and one end was inserted into the left vena jugulars externa. 50 IU/kg of heparin sodium was injected as anticoagulant, and the other tube end was inserted into the right arteria carotis communis. At this time the blood flowed from the right arteria carotis to the left vena jugulars externa via the polyethylene tube. Then normal saline solution, UK, GP6A (SEQ ID NO: 26), P6A (SEQ ID NO: 25) and KP6A (SEQ ID NO: 27) were injected in 6 min. The bolt was taken out and weighed after 1 h. The data are listed in Table 1 and Table 2, statistical data analysis was carried out by using student's t test, p<0.05 was considered significant.

TABLE 1

Thrombus Reduction with NS, UK, GP6A, and CycloGP6A

| Group | Dosage | m/mg |
| --- | --- | --- |
| NS | 3 ml/kg | 0.76 ± 7.40 |
| UK | 20,000 IU/kg | 12.81 ± 5.15[a] |
| GP6A | 5 μmol/kg | 9.31 ± 3.94[a] |
| GP6A | 10 μmol/kg | 13.17 ± 4.13[a] |
| GP6A | 20 μmol/kg | 16.81 ± 544[a,b] |
| CycloGP6A | 5 μmol/kg | 8.35 ± 2.76[a] |
| CycloGP6A | 10 μmol/kg | 17.31 ± 4.29[a] |
| CycloGP6A | 20 μmol/kg | 18.38 ± 2.08[a,b,c] | m, thrombus mass reduction;
NS, Normal Saline;
UK, Urokinase; n = 8 ;
[a]Comparing with NS, p < 0.05;
[b]Comparing with UK, p < 0.05;
[c]Comparing with 5 μmol/kg GP6A, p <0.05

TABLE 2

Thrombus Reduction with NS, UK, P6A, CycloP6A, KP6A, and CycloKP6A

| Group | Dosage | m/mg |
| --- | --- | --- |
| NS | 3 ml/kg | 0.76 ± 7.40 |
| UK | 20,000 IU/kg | 12.81 ± 5.15[a] |
| P6A | 5 μ mol/kg | 6.07 ± 2.14[a] |
| CycloP6A | 5 μ mol/kg | 10.62 ± 3.15[a] |
| KP6A | 5 μ mol/kg | 0.28 ± 2.13 |
| CycloKP6A | 5 μ mol/kg | 6.13 ± 2.31[a] |

NS, Normal Saline;
UK, urokinase; n = 8;
[a]Comparing with NS, p < 0.05;
[b]Comparing with UK, p < 0.05

From the results shown in Table 1 and 2, the thrombolytic effect among the 6 compounds, except KP6A (SEQ ID NO: 27), are close to that of the positive control group, UK, i.e., they perform excellent thrombolytic effects. As to the compounds with the same formula, the thrombolytic effect of cyclic forms is better than that of the linear form, especially GP6A. If high concentration cycloGP6A (SEQ ID NO: 30) is used (>10 μmol), the thrombolytic effect is even better than UK (2000 IU/Kg). It shows that the cyclo pentapeptides of the present invention do exhibit excellent thrombolytic effect, which is better than thrombolytic effect of UK.

At the same time, the inventor also found out that transforming the structure of peptide 6A and its analogues from linear form to cyclic forms does increase their half-life, which in turn prolongs the pharmaceutical effect in vivo; the finding is in accordance with the thrombolytic experiments described above. Therefore, the cyclic peptides of the present invention significantly mitigate the disadvantage, e.g. rapid degradation of peptide 6A, in the prior art, and serves as a medicine with long-term thrombolytic potency. Besides, the cyclic peptides of the present invention can be further applied to treat many embolism diseases, such as coronary thrombosis, cerebral artery embolism, and phlebitis. The peptide 6A of the prior art already exhibits the thrombolytic effect and serves to reduce blood pressure, extend blood vessel diameter, while the high stability of the cyclic peptide of the present invention exhibits even better ability to treat vascular sclerosis, heart disease, myocardial infarction, stroke and high blood pressure.

Although the present invention has been explained in relation to its preferred embodiment, it is to be understood that many other possible modifications and variations can be made without departing from the scope of the invention as hereinafter claimed.

What is claimed is:

1. A cyclic peptide of the formula (I):

cyclo(Xaa-Arg-Pro-Ala-Lys)                                    (I)

wherein Xaa is Ala, Gly, Glu, Gln, Asp, Asn, Arg, or Lys.

2. The cyclic peptide of claim 1, wherein said cyclic peptide is prepared by solid phase synthesis.

3. The cyclic peptide of claim 1, wherein said cyclic peptide is prepared by solution synthesis.

4. The cyclic peptide of claim 1, wherein said cyclic peptide and its pharmaceutically acceptable salts exhibit thrombolysis function.

5. The cyclic peptide of claim 1, wherein said cyclic peptide and its pharmaceutically acceptable salts are used as thrombolytic drugs.

6. The cyclic peptide of claim 1, wherein said cyclic peptide and its pharmaceutical acceptable salts are used as vasodilators.

7. A method for preparing cyclic peptides of the formula (I) (SEQ ID NO: 1):

cyclo(Xaa-Arg-Pro-Ala-Lys)                                    (I)

wherein Xaa is Ala, Gly, Glu, Gln, Asp, Asn, Arg, or Lys, including steps as follows:

(A) providing a peptide with N-terminal protecting groups, wherein at least one peptide is selected from the group consisting of

```
B - Xaa - Arg(T) - Pro - Ala - Lys(Z') - OH      (SEQ ID NO: 2),
B - Arg(T) - Pro - Ala - Lys(Z') - Xaa - OH      (SEQ ID NO: 3),
B - Pro - Ala - Lys(Z') - Xaa - Arg(T) - OH      (SEQ ID NO: 4),
B - Ala - Lys(Z') - Xaa - Arg(T) - Pro - OH      (SEQ ID NO: 5),
B - Lys(Z') - Xaa - Arg(T) - Pro - Ala - OH      (SEQ ID NO: 6);
``` wherein Xaa is Ala, Gly, Glu, Gln, Asp, Asn, Arg or Lys; B is the N-terminal protecting group of the peptide chain; Z is the side chain protecting group of Lys residue; and T is the side chain protecting group of Arg residue;

(B) adding p-nitrophenol, organic solvents and coupling agents to activate the C-terminal group of said peptide and to form a first intermediate;

(C) deprotecting the N-terminal group of said first intermediate to form a second intermediate;

(D) dissolving said second intermediate in organic solvents to perform the intramolecular cyclization of said second intermediate to form a third intermediate; and (E) removing the protecting groups on the side chains of Lys and Arg residue to form a final compound.

8. The method of claim 7, wherein at least one protecting group B in step (A) is selected from the group consisting of Boc, Fmoc, Z, Adoc, Bpoc, Trt, and Nps; at least one protecting group Z' on the side chain of Lys residue is selected from the group consisting of 4-ClZ, 2-ClZ, 2,4-Cl$_2$Z, 3,4-Cl$_2$Z, 3-ClZ, 2,6Cl$_2$Z, Boc, Tos and Cu; and, at least one protecting group T on the side chain of Arg residue is selected from the group consisting of Tos, NO$_2$, Z, Z$_2$, Mbs, Mts, Boc, and Adoc.

9. The method of claim 7, wherein at least one organic solvent used in step (B) and step (D) is selected from the group consisting of THF, Dioxane, DMF, DMSO, ethyl acetate, dichloromethane, and trichloromethane.

10. The method of claim 7, wherein at least one coupling agents used in step (B) is selected from the group consisting of DCC, HOBt, HONb, and HOSu.

11. The method of claim 7, wherein said deprotecting reaction in step (C) is performed by reacting said first intermediate with first coupling agents, wherein at least one first coupling agent is selected from the group consisting of HCl/ethyl acetate, HCl/dichlorohexane, trifluoroacetic acid, H$_2$/Pd, C, and pyridine.

12. The method of claim 7, wherein said cyclization reaction in step (D) is performed by adding at least one compound selected from the group consisting of Na$_2$CO$_3$, NaHCO$_3$, K$_2$CO$_3$, KHCO$_3$, TEA, NH$_3$, and NMM.

13. The method according to claim 7, wherein said deprotecting reaction in step (E) is performed by reacting said third intermediate with second deprotecting agent, wherein at least one of said second deprotecting agents is selected from the group consisting of hydrofluoric acid, triflouroacetic acid-trifluoromethyl sulfosilic ester, H$_2$/Pd, and C.

14. The method of claim 7, wherein said cyclic peptides and their pharmaceutically acceptable salts exhibit thrombolysis function.

15. The method of claim 7, wherein said cyclic peptides and their pharmaceutically acceptable salts are used as thrombolytic drugs.

16. The method of claim 7, wherein said cyclic peptides and their pharmaceutically acceptable salts are used as vasodilators.

17. A method for preparing cyclic peptides of the formula (I) (SEQ ID NO: 1):

cyclo(Xaa-Arg-Pro-Ala-Lys)                                    (I)

wherein Xaa is Ala, Gly, Glu, Gln, Asp, Asn, Arg, or Lys, including steps as follows:

(A) providing at least one peptide with N-terminal protecting groups, wherein at least one peptide is selected from the group consisting of

```
B-Xaa-Arg(T)-Pro-Ala-Lys(Z')-OH,      (SEQ ID NO: 2)

B-Arg(T)-Pro-Ala-Lys(Z')-Xaa-OH,      (SEQ ID NO: 3)

B-Pro-Ala-Lys(Z')-Xaa-Arg(T)-OH,      (SEQ ID NO: 4)

B-Ala-Lys(Z')-Xaa-Arg(T)-Pro-OH,      (SEQ ID NO: 5)

B-Lys(Z')-Xaa-Arg(T)-Pro-Ala-OH;      (SEQ ID NO: 6)
``` wherein Xaa is Ala, Gly, Glu, Gln, Asp, Asn, Arg or Lys; B is the N-terminal protecting group of the peptide chain; Z is the side chain protecting group of Lys residue; and T is the side chain protecting group of Arg residue;

(B) dissolving said first intermediate in organic solvents and then adding coupling agents to perform direct coupling reactions, which provides a second intermediate; and (C) removing the protecting groups on the side chain of Lys and Arg residue to form a final compound.

18. The method of claim 17, wherein at least one protecting group B in step (A) is selected from the group consisting of Boc, Fmoc, Z, Adoc, Bpoc, Trt, and Nps; at least one protecting group Z on the side chain of Lys residue is selected from the group consisting of 4-ClZ, 2-ClZ, 2,4-Cl$_2$Z, 3,4-Cl$_2$Z, 3-ClZ, 2,6Cl$_2$Z, Boc, Tos and Cu; and, at least one protecting groups T on the side chain of Arg residue is selected from the group consisting of Tos, NO$_2$, Z, Z$_2$, Mbs, Mts, Boc, and Adoc.

19. The method of claim 17, wherein said deprotecting reaction in step (B) is performed by reacting said first intermediate with first coupling agents, wherein at least one first coupling agent is selected from the group consisting of HCl/ethyl acetate, HCl/dichlorohexane, trifluoroacetic acid, H$_2$/Pd, C, and pyridine.

20. The method of claim 17, wherein at least one organic solvent used in step (C) is selected from the group consisting of THF, Dioxane, DMF, DMSO, ethyl acetate, dichloromethane, and trichloromethane; and wherein at least one of said coupling agents is selected from the group consisting of DCC, HOBt, HONb, and HOSu.

21. The method according to claim 17, wherein said direct coupling reaction is performed at a pH value between 6.0 and 8.0, and at temperatures ranging from 50° C. to 90° C.

22. The method of claim 21, wherein said pH value is adjusted by alkali, wherein at least one alkali is selected from the group consisting of Na$_2$CO$_3$, NaHCO$_3$, K$_2$CO$_3$, KHCO$_3$, TEA, NH$_3$, and NMM.

23. The method of claim 17, wherein said deprotecting reaction in step (E) is performed by reacting said second intermediate with second deprotecting agent, wherein at least one of said second deprotecting agents is selected from the group consisting of hydrofluoric acid, triflouroacetic acid-trifluoromethyl sulfosilic ester, H$_2$/Pd, and C.

24. The method of claim 17, wherein said cyclic peptides and their pharmaceutically acceptable salts exhibit thrombolysis function.

25. The method of claim 17, wherein said cyclic peptides and their pharmaceutically acceptable salts are used as thrombolytic drugs.

26. The method of claim 17, wherein said cyclic peptides and their pharmaceutically acceptable salts are used as vasodilators.

* * * * *